US 9,469,978 B2

(12) United States Patent
Chan

(10) Patent No.: US 9,469,978 B2
(45) Date of Patent: Oct. 18, 2016

(54) EXPOSED SHOWER SYSTEM

(76) Inventor: Chesta Chan, Hong Kong (CN)

(*) Notice: Subject to any disclaimer, the term of this patent is extended or adjusted under 35 U.S.C. 154(b) by 582 days.

(21) Appl. No.: 12/550,313

(22) Filed: Aug. 28, 2009

(65) Prior Publication Data

US 2010/0242166 A1  Sep. 30, 2010

Related U.S. Application Data

(60) Provisional application No. 61/163,345, filed on Mar. 25, 2009, provisional application No. 61/163,563, filed on Mar. 26, 2009.

(51) Int. Cl.
*E03C 1/06* (2006.01)
*E03C 1/04* (2006.01)
*E03C 1/046* (2006.01)

(52) U.S. Cl.
CPC ............. *E03C 1/0408* (2013.01); *E03C 1/046* (2013.01)

(58) Field of Classification Search
USPC .................................. 4/601, 570, 615, 600
See application file for complete search history.

(56) References Cited

U.S. PATENT DOCUMENTS

| 743,623 | A | * | 11/1903 | Dinneen | 4/601 |
| 1,616,514 | A | * | 2/1927 | Swimmer | 4/570 |
| 3,802,422 | A | * | 4/1974 | Hurst | 601/160 |
| 3,971,074 | A | * | 7/1976 | Yxfeldt | 4/570 |
| 4,573,639 | A | * | 3/1986 | Logue | 239/428.5 |
| 6,813,787 | B2 | * | 11/2004 | Rosenberg | 4/601 |
| 6,859,955 | B2 | * | 3/2005 | Hudson | 4/601 |
| 2002/0144341 | A1 | | 10/2002 | Zieger | |
| 2007/0056639 | A1 | * | 3/2007 | McNerney | 137/597 |

FOREIGN PATENT DOCUMENTS

GB  2315212 A  1/1998

* cited by examiner

*Primary Examiner* — Lauren Crane
(74) *Attorney, Agent, or Firm* — Koppel, Patrick, Heybl & Philpott

(57) ABSTRACT

A shower system of exposed type is disclosed, comprising a main flow passage connected to a water supply; at least two conduits which are in communication with the main flow passage and connected in pair and horizontally to two sides of the main flow passage; at least two shower spray spouts in communication with the at least two conduits, and the shower spray spouts being carried at respective outer ends of the conduits; wherein the conduits are arranged such that the shower spray spouts are in a 180° counter sit relationship with respect to the main flow passage and are combined with the conduits to define a shower stall.

15 Claims, 17 Drawing Sheets

EXPOSED SHOWER SYSTEM

RELATED APPLICATION

This non-provisional application claims priority from provisional application No. 61/163,345 filed on Mar. 25, 2009, and provisional application No. 61/163,563 filed on Mar. 26, 2009, the disclosures of which are incorporated herein by reference in their entirety.

FIELD OF THE INVENTION

This invention relates generally to a shower network system and, more particularly, to a pre-fabricated and exposed shower system which can be installed and maintained rapidly and economically in a bath room.

BACKGROUND OF THE INVENTION

Currently available multi-output shower apparatuses are the type of in-wall designs. These shower apparatuses are installed in a manner that pipes and fittings of the apparatuses are wall embedded with only jet sprays exposed for water coming out at an angle of 90° with respect to a surface of the wall. FIGS. 1 and 2 illustrate a shower apparatus of this type, wherein all the piping network structures are installed behind the walls of a bath room with spray spouts being exposed, and wherein the shower heads 1 are all at an angle of 90° with respect to a surface 2 of the wall.

The in-wall shower apparatuses are associated with the following drawbacks:
  expertise and specialized consultation are required in terms of installation and maintenance of the apparatuses, which is costly and time-consuming; and
  existing wall and furnished surface need to be destroyed at installation in order to distribute new piping layout to the in-wall water supply, relevant cement and plumbing work creates harassment in noise and environmental disturbance.

There are also multi-output shower apparatuses available in panel or column shape designs, for example, in U.S. Patent Application No. 2002/0144341A and UK Patent Application No. 2315212A. These apparatuses provide all the jet spray outputs from their panel or column shaped surfaces. Like the shower apparatuses of in-wall designs, the shower heads 1 of this type are all at an angle of 90° with respect to a surface 2 of the wall parallel to the panel or column 3, as shown in FIG. 3.

U.S. Patent Application No. 2002/0144341A discloses a shower system for providing automated control over both water temperature and pressure for a plurality of shower heads or other sources of water, wherein the shower heads are all at an angle of 90° with respect to a surface of the wall. In this patent application, the housing for containing the electrical mechanical elements of this system is dimensioned such that the housing will fit within the cavity of the typical wall.

UK Patent Application No. 2315212A discloses a shower apparatus in the form of a shower column, comprising a plurality of shower heads each attached to respective conduit means, which are in communication with a mixing means and a diverter means for diverting water to the shower heads. In this patent application, the shower apparatus is configured to be in the form of a shower column in which all the elements of this apparatus is housed.

The shower apparatuses of panel or column shape designs are associated with the drawback that they only provide a single direction jet shower environment and the user cannot attain a two-side body shower. Due to the arrangement of the shower heads at an angle of 90° relative to the wall surface, a lot of water is spread widely and thus wasted during the process of showering.

While a variety of shower systems are known in the art to fulfill their respective, particular objectives and requirements, for example, the shower systems mentioned above, none are available which provide the user with the ease and simplicity of installation and maintenance of the shower system and with an invigorating and refreshing shower experience, such as is the subject of the present invention.

Therefore, there exists a need for a shower system which is able to provide a user with the ease for installation and maintenance, a full body water therapy experience to the face, mouth, body and foot for comfort and potential health benefits.

SUMMARY OF THE INVENTION

The present invention has been developed to fulfill the need noted above and therefore has a principle object of the provision of a shower system that is able to provide a user with a cost and time effective solution.

Another object of the invention is to provide a shower system that provides easier and cheaper installation and maintenance.

A further object of the invention is to provide a shower system that is water conserving but providing an invigorating and more refreshing experience of using the shower system.

A yet another object of the invention is to provide a shower that provides a user with a full body water therapy experience exclusively to the face, mouth, body and feet for comfort and potential health benefits in daily life.

These and other objects and advantages of the invention are satisfied by providing a shower system comprising:
  a main flow passage connected to a water supply;
  at least two conduits which are in communication with the main flow passage and connected in pair and horizontally to two sides of the main flow passage;
  at least two shower spray spouts in communication with the at least two conduits, and the shower spray spouts being carried at respective outer ends of the conduits;
  wherein the conduits are arranged such that the shower spray spouts are in a 180° counter sit relationship with respect to the main flow passage and are combined with the conduits to define a shower stall.

In one preferred embodiment of the invention, the outer end of each of the at least two conduits is connected to a "T"-shaped tube or a "S"-shaped tube on which the shower spray spouts corresponding to shoulders, waist and thighs of the user are arranged.

In another preferred embodiment of the invention, the system comprises six conduits symmetrical about the main flow passage to horizontally form 3 pairs of conduits and positioned at different vertical heights so as to correspond to shoulders, waist and thighs of the user, respectively.

According to the invention, the shower system preferably comprises a facial spray spout in communication with and disposed at an upper part of the shower system, and a mouth spray spout adjacent to the facial spray to provide mouth and gum care to the user. More preferably, the shower system further comprises an overhead shower spray spout, and a foot spray spout in communication with and disposed at an lower part of the shower system. Of course, the shower system may be used with a footbath shower tray or a bath tray in existence, which has an adjustable overflow drainage for providing a foot bath.

1. In a preferred embodiment of the invention, the shower system comprises a diverter means installed on and in communication with the main flow passage for controlling the spray spouts to out-flow water individually or simultaneously and/or for controlling a temperature of the outflow water. Advantageously, the diverter means comprises a diverter having a plurality of outputs for directing water to the corresponding spray spouts individually or simultaneously, and a built-in venturi injection mechanism connected to an input of the diverter for introducing air, health care fluids or health care powders to blend with water flowing into the diverter, allowing for improving a pressure of water and providing a healthy and refreshing shower. Alternatively, at each output of the diverter is disposed a venturi injection mechanism for introducing air, health care fluids or health care powders, and in this case, the venturi injection mechanism can be used to direct water output individually to one of the spray spouts corresponding to the head, the face, the mouth, the shoulders, the waist, the thighs and the feet, or to a combination of two or more of these spray spouts.

In another preferred embodiment of the invention, the shower system comprises a mixing valve through which hot and cold water sources flow into the main flow passage. The mixing valve may be included in the diverter means to keep communication with the built-in venturi injection mechanism.

For the aesthetic appearance, a housing is provided to receive the main flow passage, the diverter means, the mixing valve and other parts of the shower system. While the health care fluids or the health care powders may be supplied from a dispenser arranged on the housing where appropriate.

According to the invention, the shower spray spouts are able to rotate by 45° and adjustable for their angles. The shower spray spouts is preferably further provided with a massage function.

The main flow passage can be adjustable vertically for its height to satisfy the preference of a user.

According to the invention, the connections among the conduits and the main flow passage are accomplished in a threaded manner or in a snap-in manner.

Generally speaking, the shower system of the invention is prefabricated as one piece.

To have a better understanding of the invention reference is made to the following detailed description of the invention and embodiments thereof in conjunction with the accompanying drawings.

BRIEF DESCRIPTION OF THE DRAWINGS

In the various figures of the drawings, like reference numbers are used to designate like parts.

DETAILED DESCRIPTION OF THE PREFERRED EMBODIMENTS

Figure 1:
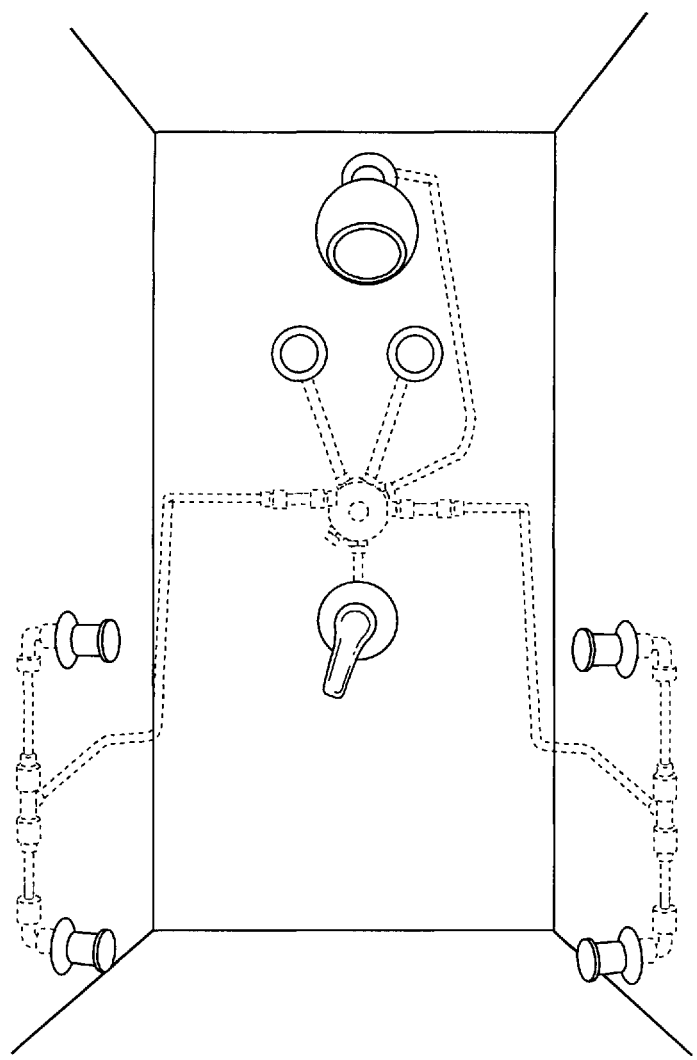
FIG. 1 is a perspective view of a shower system of in-wall design of the prior art wherein all the piping network structure are installed behind the walls of a bath room with spray spouts protruding beyond surfaces of the walls.

Several shower systems embodying the principles and concepts of the present invention will be described with reference to the drawings and particularly to FIGS. 4-23 thereof. While this invention is illustrated and described in preferred embodiments, the shower system may be produced in many different configurations, forms and materials.

Referring firstly to FIGS. 4-7 of the drawings, a shower system 10 constructed consistent with a first embodiment of the invention is illustrated. The shower system 10 is a completely pre-fabricated one-piece piping network structure and comprises a main flow passage 100 connected directly to a standard water supply point, such as a water faucet (not shown) which provides a blend of hot and cold water. The shower system 10 comprises an overhead shower spray spout 110, a facial shower spray 120, a mouth spray spout 130, body spray spouts 140, 150, 160 respectively in pair corresponding to shoulders, waist and thighs of a user, and a foot spray spout 170.

Figure 2:
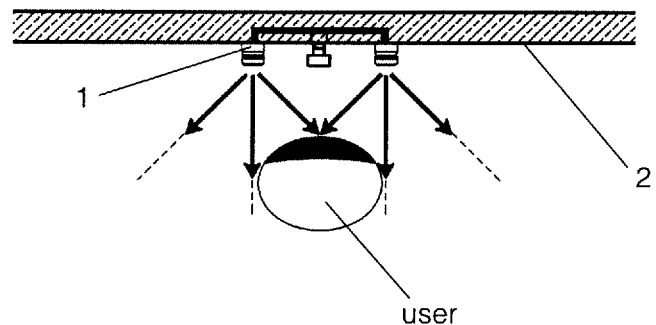
FIG. 2 is a schematic view of the shower system of FIG. 1 showing that the spray spouts are at an angle of 90° relative to the wall surface on which the spray spouts are mounted in front of the user.
Figure 3:
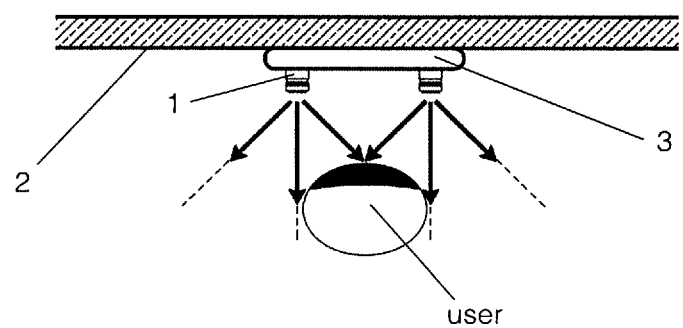
FIG. 3 is a schematic view of the shower system of panel or column shape design showing that the spray spouts are at an angle of 90° relative to the wall surface parallel to the panel or column.
Figure 6:
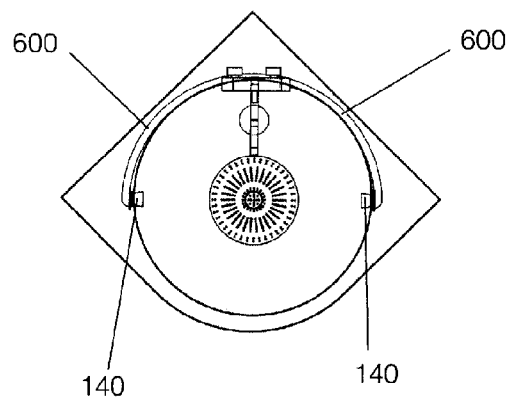
FIG. 6 is a top view of the shower system shown in FIG. 4.
Figures 4, 5:
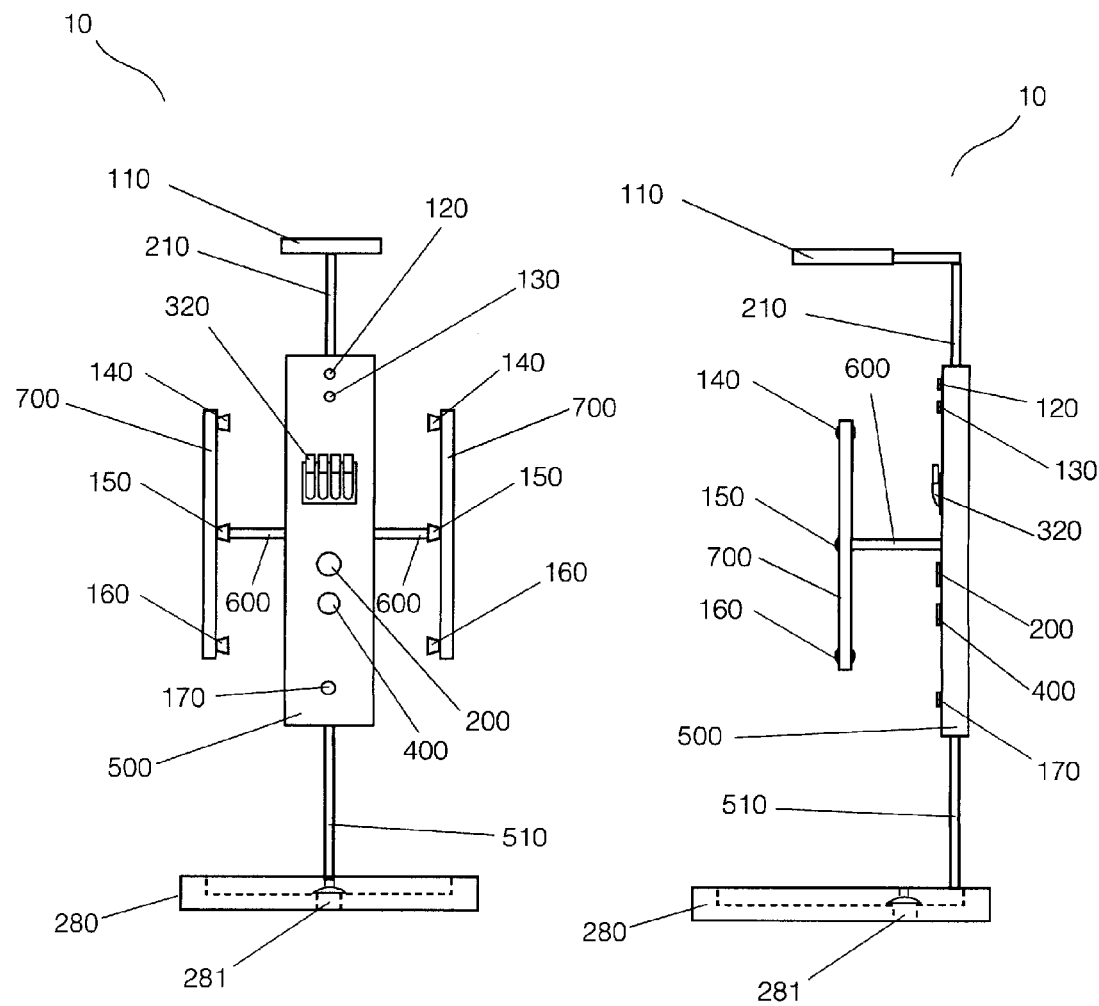
FIG. 4 is a front view of a shower system consistent with a first embodiment of the invention.
FIG. 5 is a right side view of the shower system shown in FIG. 4.

In this embodiment, two conduits 600 are in communication with and connected horizontally to the main flow passage 100. Each of the conduits 600 is connected communicatively at its outer end to a "T"-shaped tube 700 on which the body spray spouts 140, 150, 160 are carried. The conduits 600, the "T"-shaped tube 700 and the body spray spouts 140, 150, 160 are arranged so as to form a semi-surrounded body spray piping structure to define a shower stall, which is shown in more details in FIG. 6. FIG. 6 also clearly illustrates that the body spray spouts are in a 180° counter sit position with respect to the main flow passage. This design is very much different from the shower system available in the art, such as the one shown in FIGS. 2 and 3. According to the invention, such a semi-surrounded body spray piping structure and the 180° counter sit body spray spouts allow the user to receive water across both sides of the body in an equal manner and greater equilibrium comfort when taking a shower.

Figure 7:
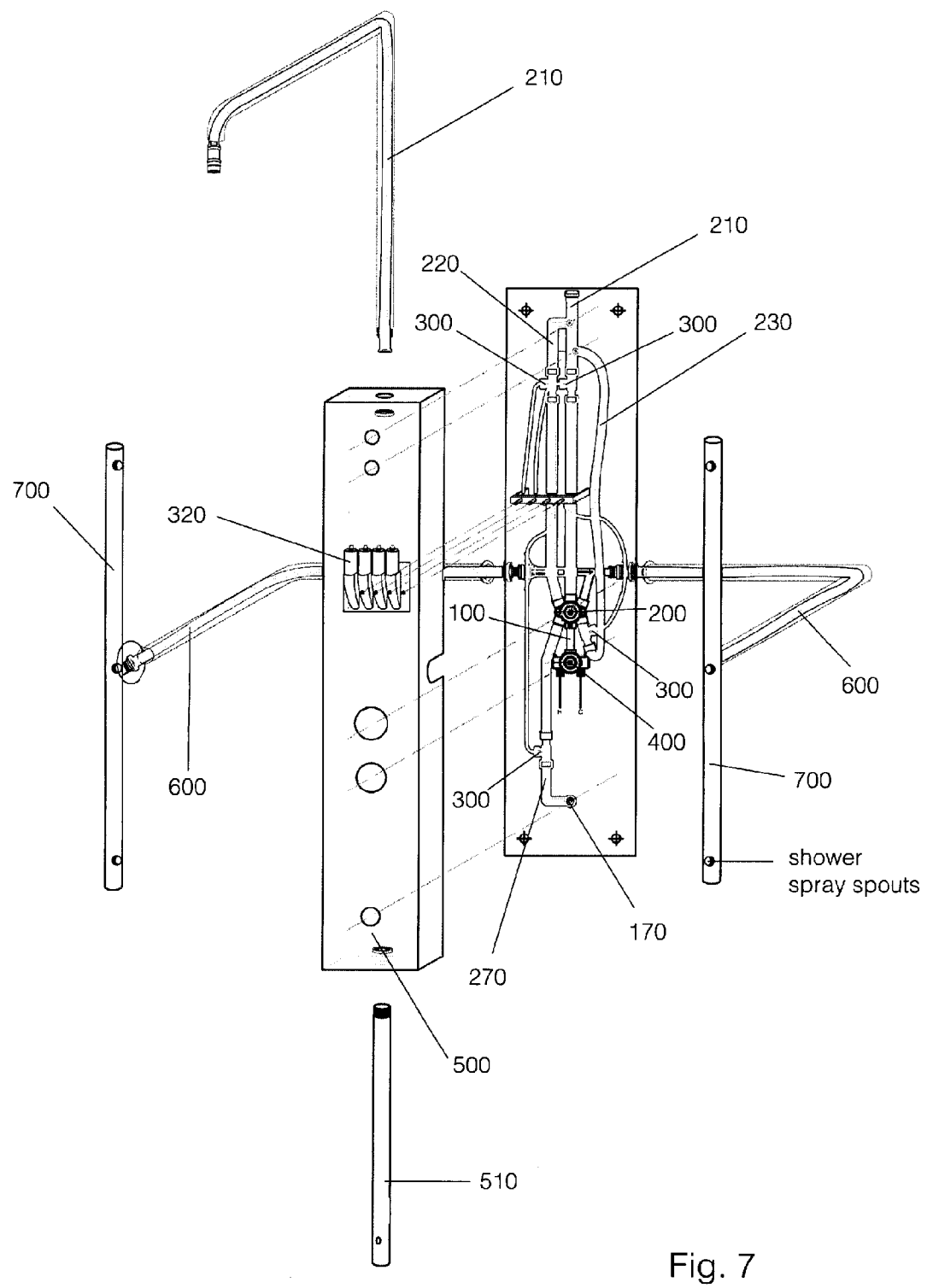
FIG. 7 is an exploded view of the shower system shown in FIGS. 4 to 6.
Figure 8:
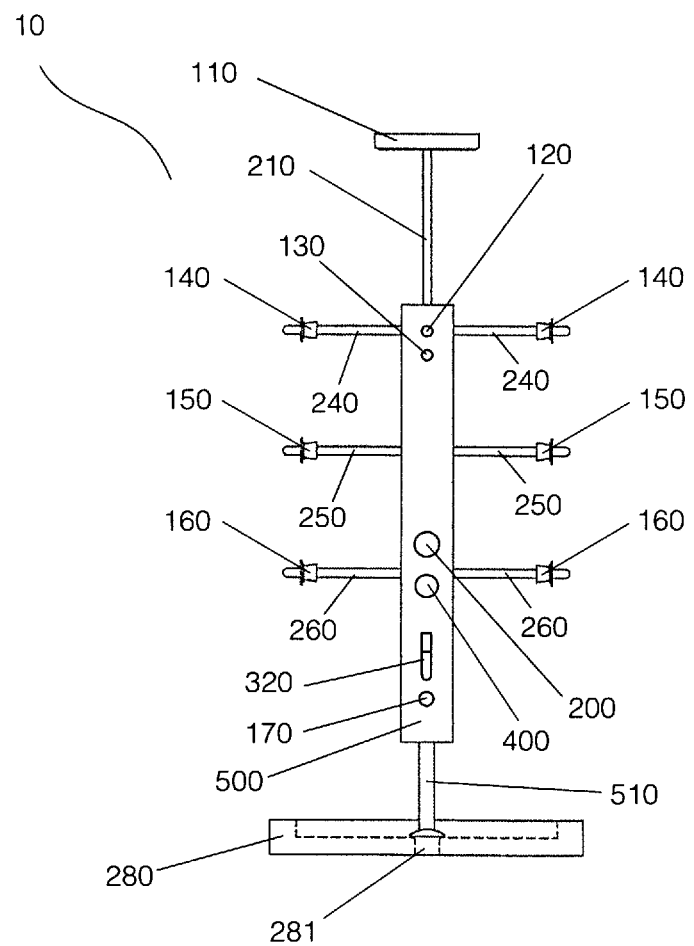
FIG. 8 is a front view of a shower system consistent with a second embodiment of the invention.
Figure 9:
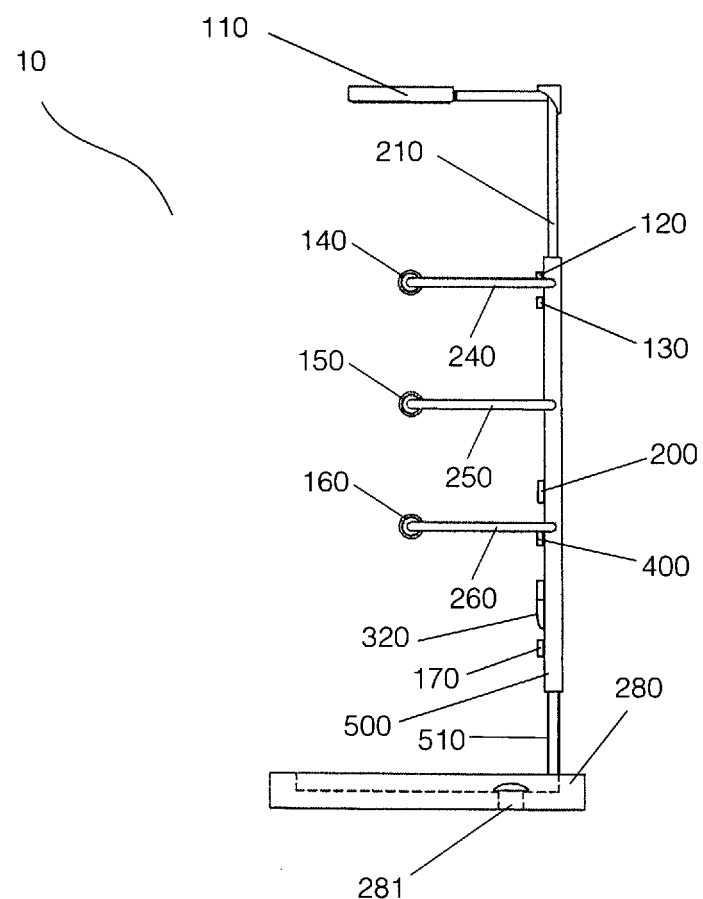
FIG. 9 is a right side view of the shower system shown in FIG. 8.
Figure 10:
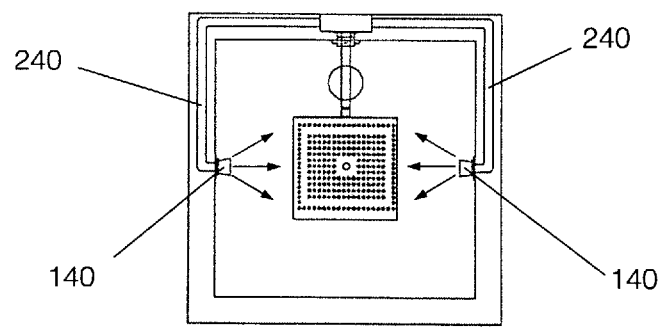
FIG. 10 is a top view of the shower system shown in FIG. 8.

The overhead shower spray spout 110 is carried at an outer end of a first conduit 210, the facial spray spout 120 is carried at an outer end of a second conduit 220, the mouth spray spout 130 is carried at an outer end of a flexible hose 230 to allow it to be pulled out to provide mouth and gum care to the user, and the foot spray spout 170 is carried at an outer end of a sixth conduit 270. With reference to FIG. 7, all the conduits 210, 220, 230, 270, 700 are in communication with different outputs of a diverter 200. These conduits may be selected from solid pipes, or flexible pipes of smaller sizes are installed within these solid pipes to improve water flow and increase water pressure when necessary, as illustrated in FIG. 7.

The facial spray sprout 120 is mounted to provide the user to receive aerated hot water in vapor and misty form directable to his face. The mouth spray spout 130 is mounted to provide a mouth wash or gum care massage with a stronger water output, allowing the user to have a daily potential health benefit. The mouth spray spout 130 is connected to a pull-out flexible hose that provides flexibility to the user at different heights.

The foot spray sprout 170 is mounted to provide individual water output for foot wash. In this embodiment, the shower system 10 is used with a shower tray 280 or bath tub available in a bathroom at the bottom of this system to allow for a foot bath by adding salts or other foot therapy products to soak the feet when taking a shower. An overflow drainage 281 is elevated above from the bottom of the shower tray 280 or bath tub by 4 cm to 10 cm in order to lead the drainage water to the conventional waste with a plastic tube.

A separate housing 500 of rectangular configuration made from a material selected from stainless steel, brass, aluminum, plastic or synthetic material, for example, is provided in the embodiment to receive the conduits directed to the facial spray spout, the mouth spray spout and the foot spray sprout as well as the diverter 200. Referring to FIG. 7, a corresponding number of openings through which the spray sprouts pass are formed on a front panel of the housing 500. The bottom of the housing 500 is coupled to a post 510 which can be adjusted vertically for its height and thus for the height of the shower system 10 to satisfy the preference of the user, which would be within the ability of a person skilled in the art.

As shown in FIG. 7, the diverter 200 is installed on the main flow passage 100 for controlling the water output of the spray spouts, which allows water output either to the spray spouts directed to the head, the face, the mouth and the feet individually or to the spray spouts directed to the shoulder, waist and thighs at both sides of the user. In this embodiment, a mixing valve 400 has one end connected to the hot and cold water sources and the other connected to an input of the diverter 200. As illustrated, a venturi injection mechanism 300 is installed on each of the conduits 210, 220, 230, 270, 700.

The diverter 200 is of the multi-way type for controlling individual water output of the spray spouts. Dialing the diverter 200 permits the user to select water output from the mixing valve 400 through the conduits to the selective outlet: i.e. the overhead shower spray 110, the facial shower spray 120, the mouth shower spray 130, the body shower sprays 140, 150, 160, or the foot shower spray 170, with the result of receiving a fully customizable shower experience.

The venturi injection mechanism 300 is provided to create suction of fresh air, health care fluids or health care powders into water when the water passes through the venturi injection mechanism. FIG. 7 shows that the venturi injection mechanisms 300 are engaged with a dispenser 320 of health care fluids or health care powders. The dispenser 320 is arranged on the housing 500 and includes a plurality of containers, each of the containers are in communication with the respective venturi injection mechanism 300. By use of the venturi injection mechanisms 300, the health injection fluids or powders can be mixed with the water to provide a refreshing shower experience.

The mixing valve 400 may be of a conventional type and is connected to hot and cold water sources for controlling the output volume and the temperature of water to suit the user's requirement. The mixing valve is well known in the art and not the essence of the invention, and therefore is not elaborated herein.

As described above, the shower system 10 is prefabricated as one piece. According to the invention, the connections among all parts of the shower system 10, including the conduits and the main flow passage may be connected in a threaded manner or in a snap-in manner.

Referring now to FIGS. 8 to 11, a shower system 10 constructed consistent with a second embodiment of the invention is illustrated. The shower system 10 is a completely pre-fabricated one-piece piping network structure and comprises a main flow passage 100 connected directly to a standard water supply point, such as a water faucet (not shown) which provides a blend of hot and cold water. The shower system 10 comprises an overhead shower spray spout 110, a facial shower spray 120, a mouth spray spout 130, three rows of body spray spouts 140, 150, 160 respectively corresponding to shoulders, waist and thighs of a user, and a foot spray spout 170.

The overhead shower spray spout 110 is carried at an outer end of a first conduit 210, the facial spray spout 120 is carried at an outer end of a second conduit 220, the mouth spray spout 130 is carried at an outer end of a flexible hose 230 to allow it to be pulled out to provide mouth and gum care to the user, the body spray spouts 140, 150, 160 are carried at respective outer ends of third, fourth and fifth conduits 240, 250, and 260 which extend in pair and horizontally from two sides of the main flow passage, and the foot spray spout 170 is carried at an outer end of a sixth conduit 270. With collective reference to FIGS. 11 and 12, all the conduits 210, 220, 230, 240, 250, 260, 270 are in communication with different outputs 181, 182, 183, 184, 185 of a diverter means 180. These conduits may be selected from solid pipes, or flexible pipes of smaller sizes are installed within these solid pipes to improve water flow and increase water pressure, when necessary.

The facial spray sprout 120 is mounted to provide the user to receive aerated hot water in vapor and misty form directable to his face. The mouth spray spout 130 is mounted to provide a mouth wash or gum care massage with a stronger water output, allowing the user to have a daily potential health benefit. The mouth spray spout 130 is connected to a pull-out flexible hose that provides flexibility to the user at different heights.

In this embodiment, the third, fourth and fifth conduits 240, 250, and 260 are in communication with an output of the diverter means and correspond to the positions of shoulders, waist and thighs of the user. These conduits are shaped in a rectangular configuration and arranged so as to form a semi-surrounded body spray piping structure which defines a shower stall, as shown in more details in FIG. 10. While FIGS. 8 and 10 clearly illustrate that these conduits carry the respective spray spouts in a 180° counter sit position with respect to the main flow passage. This design is very much different from the shower system available in the art, such as the one shown in FIGS. 2 and 3. According to the invention, such a semi-surrounded body spray piping structure and the 180° counter sit body spray spouts allow the user to receive water across both sides of the body in an equal manner and greater equilibrium comfort when taking a shower. Advantageously, the body spray spouts 140, 150, 160 are configured to be able to rotate by 45° and can adjust for their angles to provide the convenience of the user.

The foot spray sprout 170 is mounted to provide individual water output for foot wash. The shower system 10 may be used in combination with a shower tray 280 or a bath tub available in a bath room at the bottom of this system to allow for a foot bath by adding salts or other foot therapy products to soak the feet when taking a shower. An overflow drainage 281 of the shower tray or the bath tub is elevated above from the bottom by 4 cm to 10 cm., in order to lead the drainage water to the conventional waste with a tube of plastic, stainless steel or brass material. Such a design provides an economical way to achieve foot bath. Accordingly, the shower system 10 enables the user to have a foot bath and take a multi-directional aerated water shower at the same time, with a great equilibrium comfort with heating and water distribution to be achieved in use.

Figure 11:
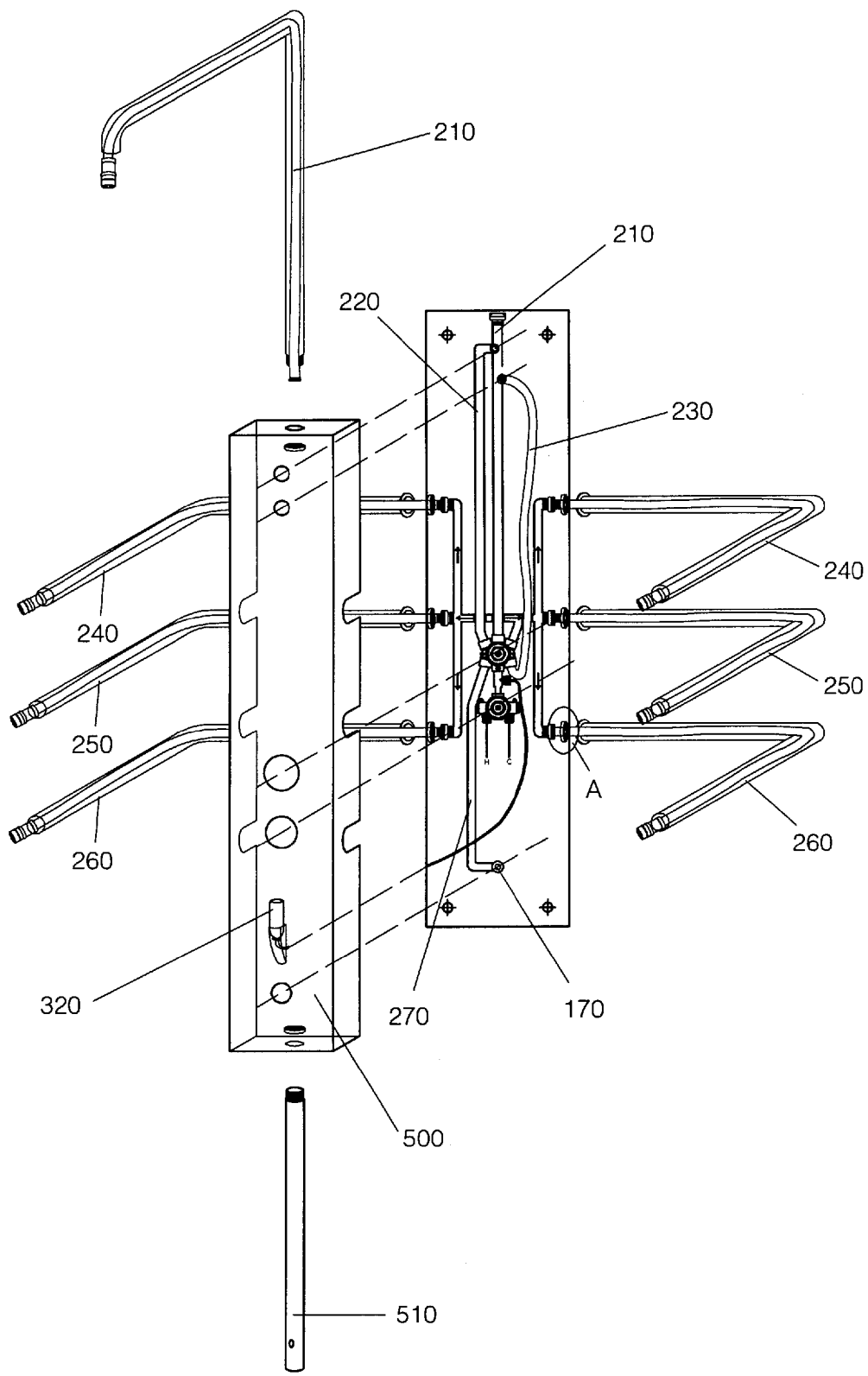
FIG. 11 is an exploded view of the shower system shown in FIGS. 8 to 10.

A separate housing 500 of rectangular configuration made from a material selected from stainless steel, brass, aluminum, plastic or synthetic material, for example, is provided in the embodiment to receive the conduits directed to the facial spray spout, the mouth spray spout and the foot spray sprout as well as the diverter means 180. Referring to FIG. 11, a corresponding number of openings through which the spray sprouts pass are formed on a front panel of the housing 500. The bottom of the housing 500 is coupled to a post 510 which can be adjusted vertically for its height and thus for the height of the shower system 10 to satisfy the preference of the user, which would be within the ability of a person skilled in the art.

Figure 12:
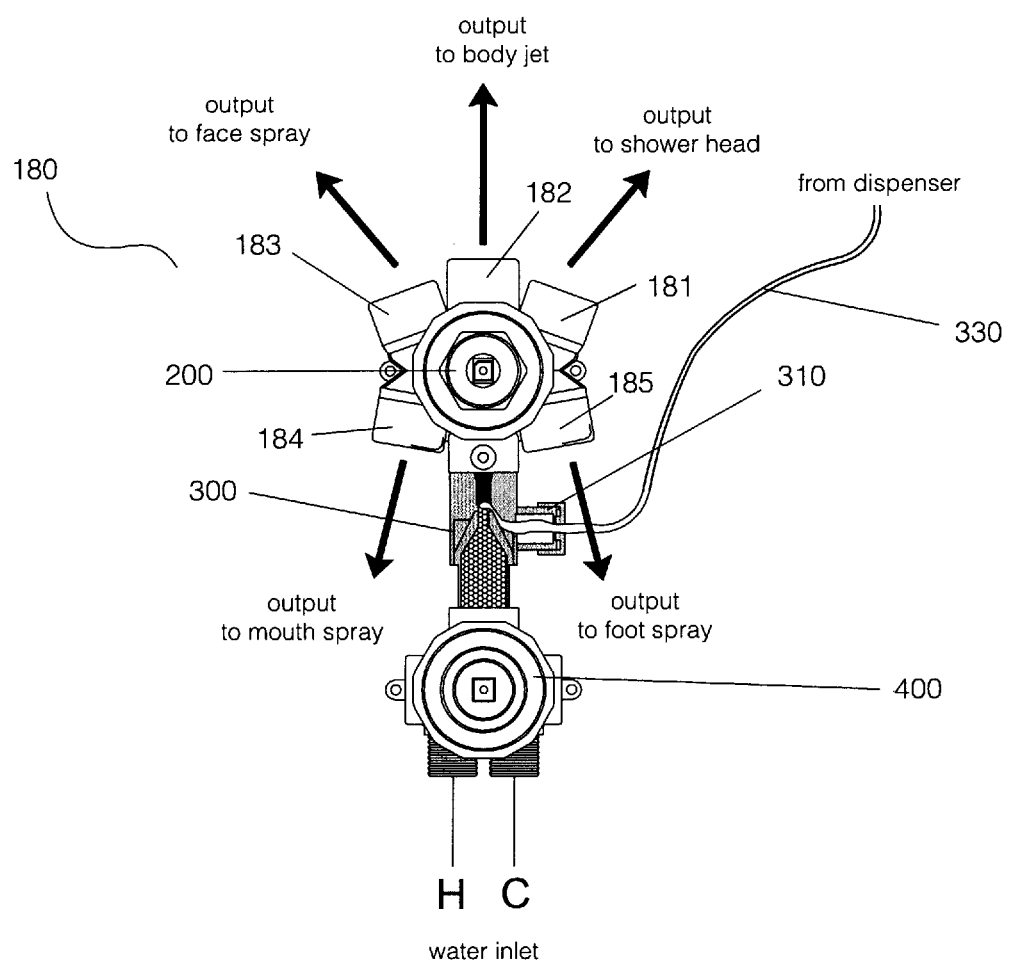
FIG. 12 is a schematic view of an example of arrangement of a diverter means with a built-in venturi injection mechanism utilized in the shower system of the invention.

As shown in FIG. 12, the diverter means 180 is installed on the main flow passage 100 for controlling the water output of the spray spouts, which allows water output either to the spray spouts directed to the head, the face, the mouth and the feet individually or to the spray spouts directed to the shoulder, waist and thighs at both sides of the user. It would be appreciated that directing the water output to a combination of two or more of spray spouts of the head, the face, the mouth, the feet and the combination of the body spray spouts at opposite angle of 180° is possible. This is different from the mechanism of the shower apparatuses in the prior art. In this embodiment, the diverter means 180 comprises a diverter 200, a built-in venturi injection mechanism 300 connected to an input of the diverter 200, and a mixing valve 400 connected to the hot and cold water sources.

The diverter 200 is of the multi-way type for controlling individual water output of the spray spouts. Dialing the diverter 180 permits the user to select water output from the mixing valve 400 through the conduits to the selective outlet: i.e. the overhead shower spray 110, the facial shower spray 120, the mouth shower spray 130, the body shower sprays 140, 150, 160, or the foot shower spray 170, with the result of receiving a fully customizable shower experience.

Figure 14A:
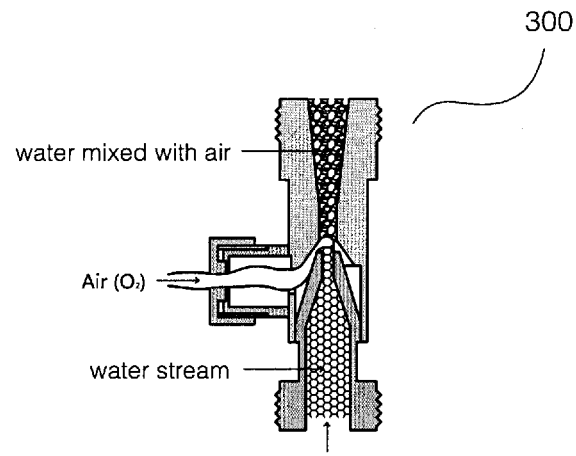
FIGS. 14A and 14B are enlarged views respectively showing air and health care fluids or powders are injected into the shower system through the venturi injection mechanism.
Figure 14B:
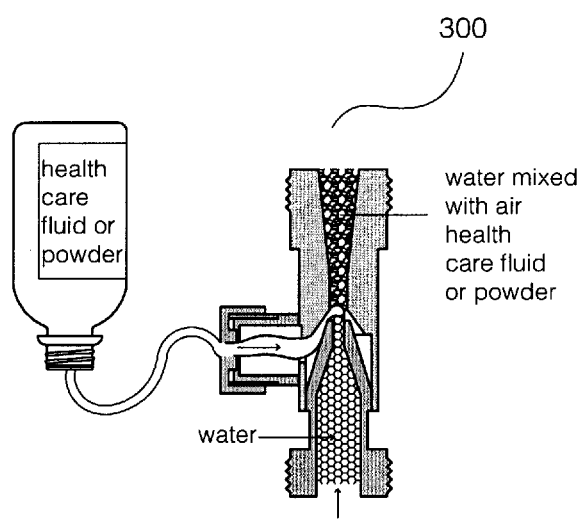

The venturi injection mechanism 300 connected to a flexible hose 330 is provided to create suction of fresh air, health care fluids or health care powders into water when the water passes through the venturi injection mechanism. FIG. 12 shows that the flexible hose 330 has one end connected to the venturi injection mechanism 300 and the other end extending beyond a flange 310 which remains open in the case of air suction or which is engaged with a dispenser 320 of health care fluids or health care powders. By use of the venturi injection mechanism 300, fresh air can be drawn into this mechanism and to the diverter 200. The capacity of air intake reduces the capacity of water inflow while maintaining the running pressure of water that comes into the diverter, thus improving the water pressure as well as increasing the water flow velocity while decreasing the flow rate of water. As shown in FIG. 14A, the fresh air is sucked into the water to produce tiny packets of oxygen bubbles that mix with water flow in the diverter 200, thereby enabling oxygenating massage to the user's body to give an invigorating, healthy and more refreshing shower. The aerated water also gives a faster and better reaction with soaps, foaming baths or bath gels. Such a design allows the user to receive a shower of better water effect while using less water and energy.

The shower system 10 also provides the user with the option of using health care fluids or powders such as relaxing shower oils, distress bath and shower products. In this case, the other end of the flexible hose 330 is engaged with the dispenser 320 which is arranged on the front panel of the housing 500, allowing for the suction of the health care fluids or powders so as to mix with water flow in the diverter 200. This would give the user to have refreshing and relaxing spirit. In view of the arrangement that the venturi injection mechanism 300 is located in the diverter means 180, the dispenser 320 has one bottle for containing the health care fluids or health care powders to be connected with the flexible hose 330.

Figure 13:
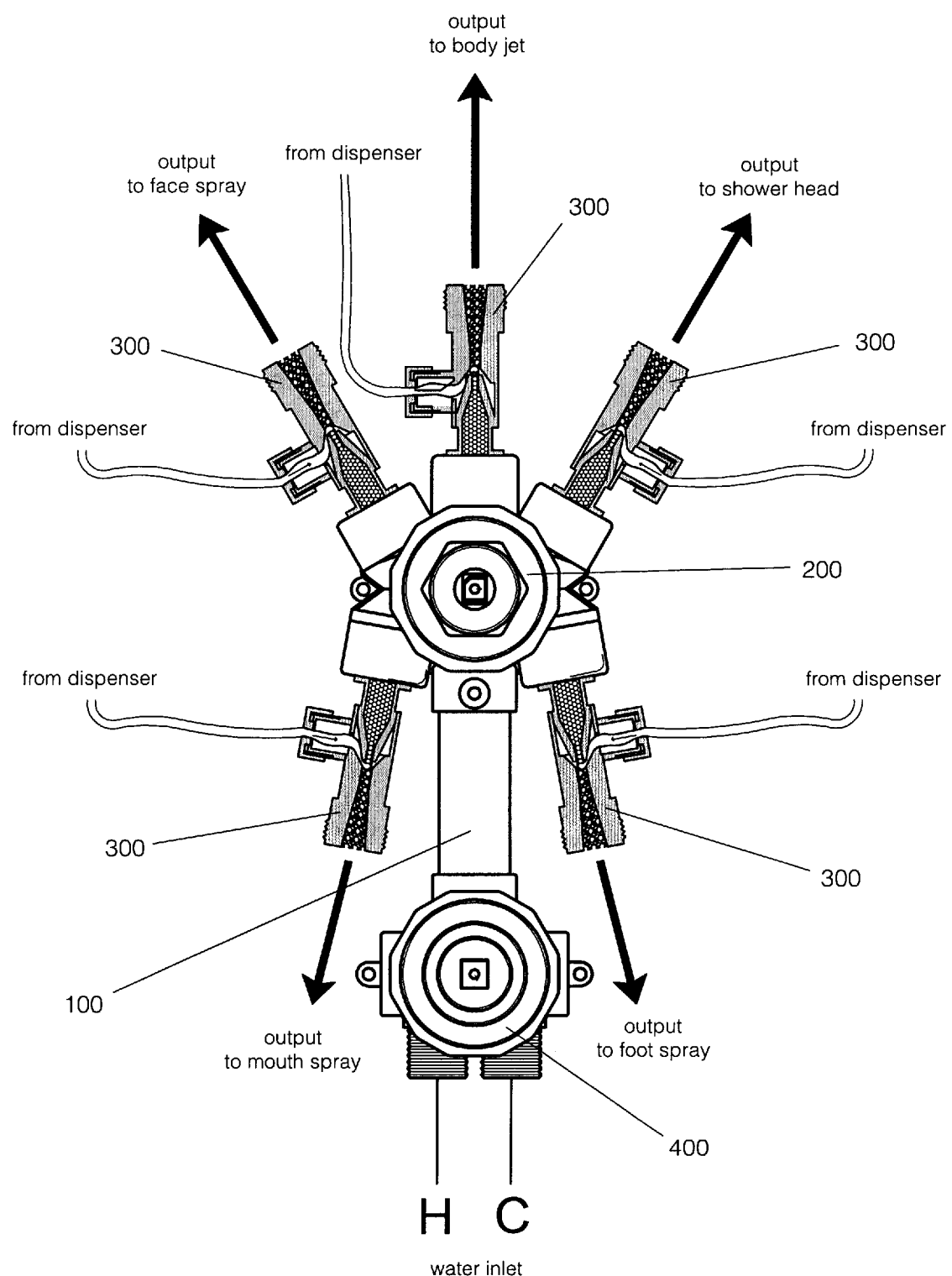
FIG. 13 is a schematic view of another example of arrangement of a diverter with a plurality of venturi injection mechanisms disposed at various output of the diverter.

Another variant of the arrangement of the venturi injection mechanism is illustrated in FIG. 13. At each output of the diverter 200 is positioned a venturi injection mechanism 300 having a flexible hose for suction of fresh air, health care fluids or health care powders. In this case, the fresh air, the health care fluids or the health care powders mix with water coming out from the diverter 200. It would be understood that the dispenser may be provided with several bottles for containing health care fluids or powders in engagement with the respective flexible hoses.

The mixing valve 400 may be of a conventional type and is connected to hot and cold water sources for controlling the output volume and the temperature of water to suit the user's requirement. In this embodiment, the mixing valve 400 is included in the diverter means 180. It would be appreciated that the mixing valve can be provided separately from the diverter means when necessary, which allows the user to remain his existing mixing valve for the best benefits in cost, if desired. The mixing valve is well known in the art and not the essence of the invention, and therefore is not elaborated herein.

Figure 23A:
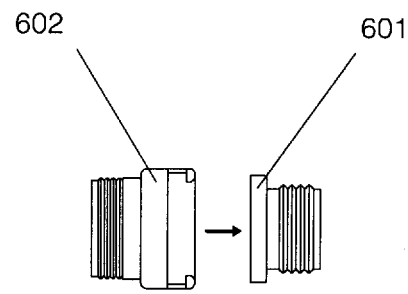
FIGS. 23A and 23B are enlarged views taken from Section "A" of FIG. 11.
Figure 23B:
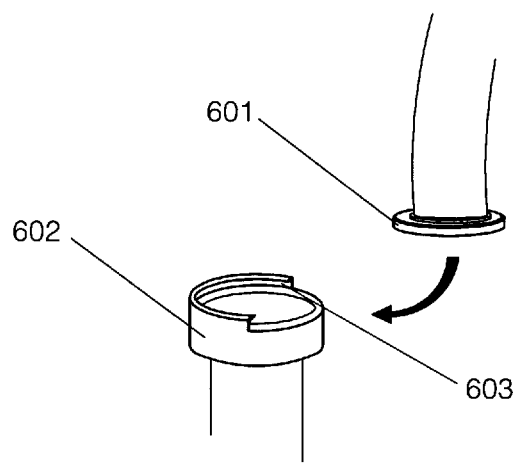

As described above, the shower system 10 is prefabricated as one piece. According to the invention, the connections among all parts of the shower system 10, including the conduits and the main flow passage may be connected in a threaded manner or in a snap-in manner. One example of the snap-in connection is shown in FIGS. 23A and 23B, in which a first piece of the conduit is fitted with a flange 601, and a second piece of the conduit is fitted with a connection member 602 having a slot 603 formed on its inner wall. The two pieces of the conduit are firmly connected by coupling the flange 601 with the slot 603 of the connection member 602.

It can be seen that a significant feature of the invention is the construction of a completely exposed type of pre-assembled shower system, which eliminates the drawbacks of the known type of in-wall designs and panel or column designs requiring for periods of time and skilled labors from various sectors, such as plumbing, constructional, electrical etc. . . . The shower system 10 is easy and rapid to install and maintain in site without the necessity of the intervention of skilled labor, which permits a saving in the cost of installation and maintenance because of a better management of the costs. This was not accomplished by the prior art shower systems/apparatuses.

Figure 15:
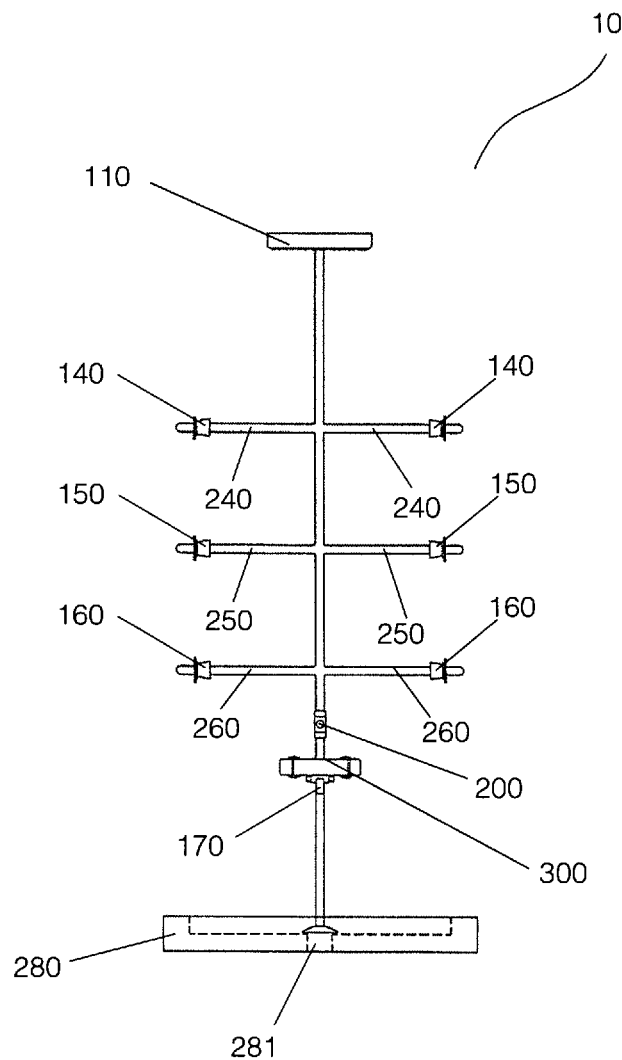
FIG. 15 is a front view of a shower system consistent with a third embodiment of the invention.
Figure 16:
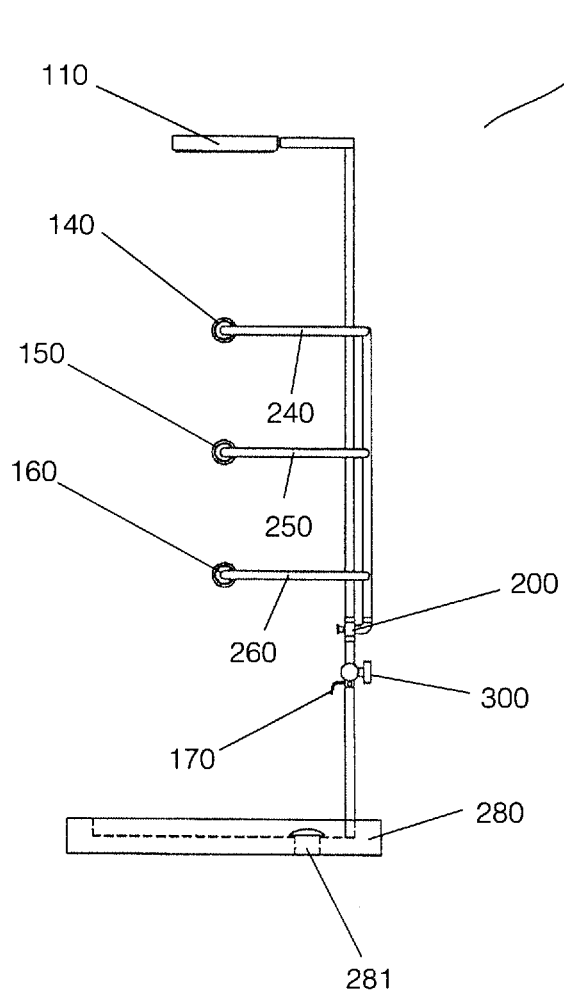
FIG. 16 is a side view of the shower system shown in FIG. 15.
Figure 17:
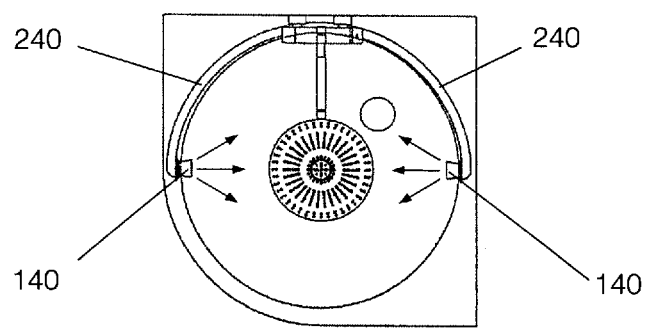
FIG. 17 is a top view of the shower system shown in FIG. 15.

Referring now to FIGS. 15 to 17, a shower system 10 consistent with a third embodiment of the invention is shown. This embodiment is similar in structure and operation to that disclosed in the first and second embodiments, but significantly differing in the following aspects:

the conduits carrying the body spray spouts are of a semicircular configuration to define a shower stall; and no housing is provided in this embodiment, the diverter 200, the venturi injection 300 and the mixing valve 300 are all disposed and in communication with the main flow passage 100.

Figure 18:
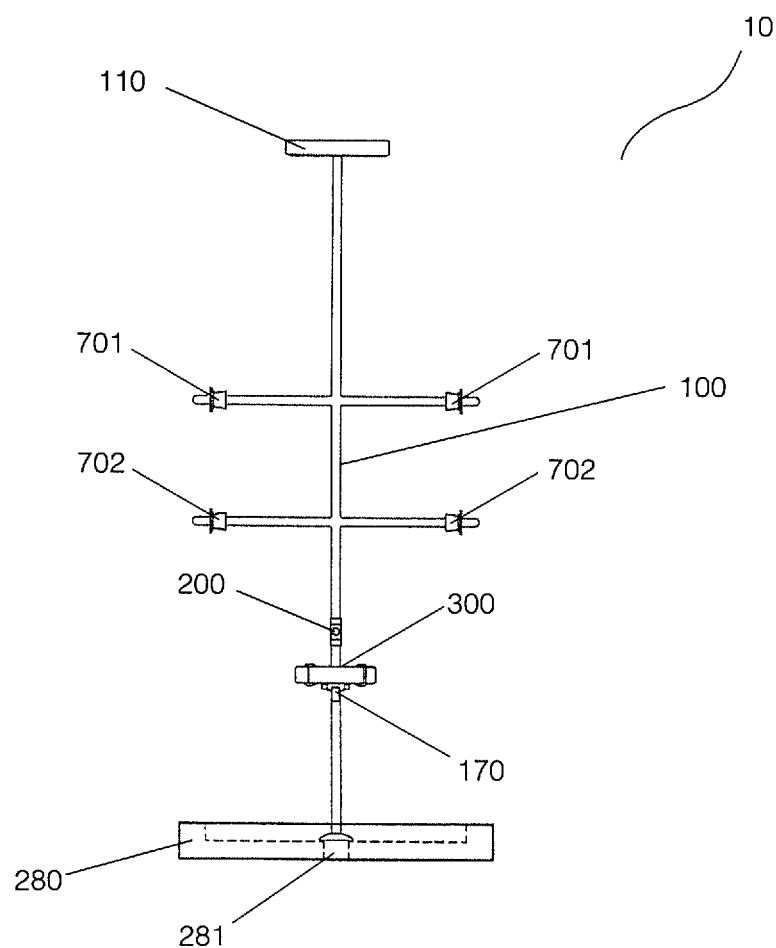
FIG. 18 is a front view of a shower system consistent with a fourth embodiment of the invention in which upper and lower body sprays are provided.
Figure 19:
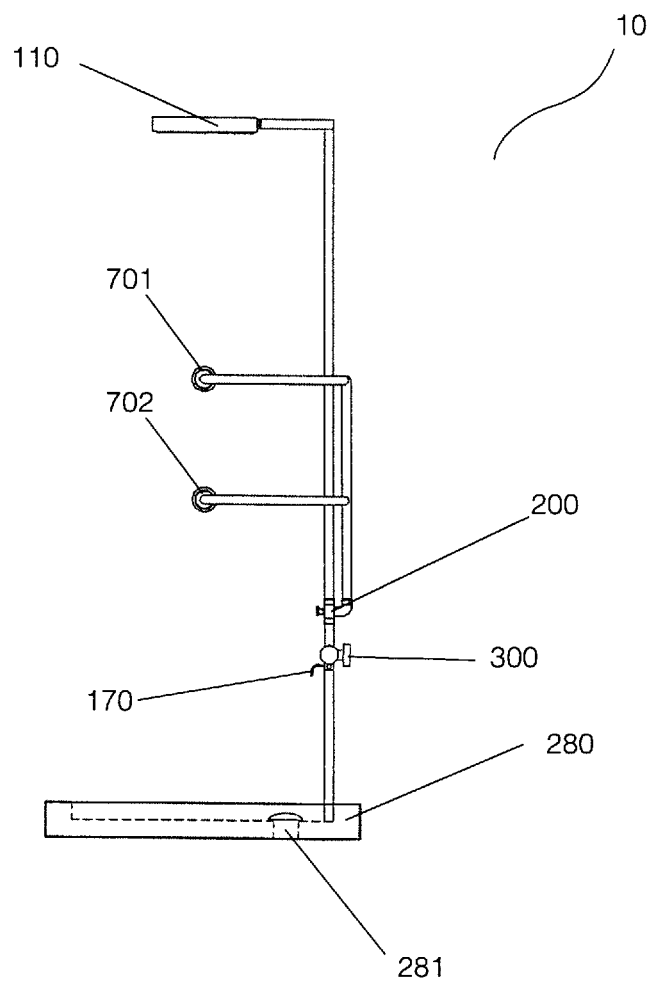
FIG. 19 is a side view of the shower system shown in FIG. 18.
Figure 20:
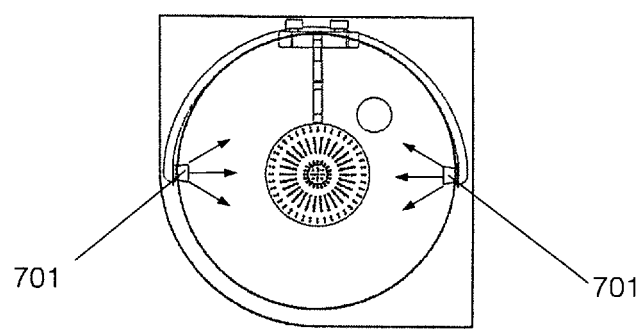
FIG. 20 is a top view of the shower system shown in FIG. 18.

FIGS. 18-20 illustrate a shower system consistent with a fourth embodiment of the invention. The embodiment is similar in structure and operation to that disclosed in the third embodiment, except that two rows of spray spouts 701 and 702 respectively corresponding to the upper body and the lower body of the user are provided.

Figure 21:
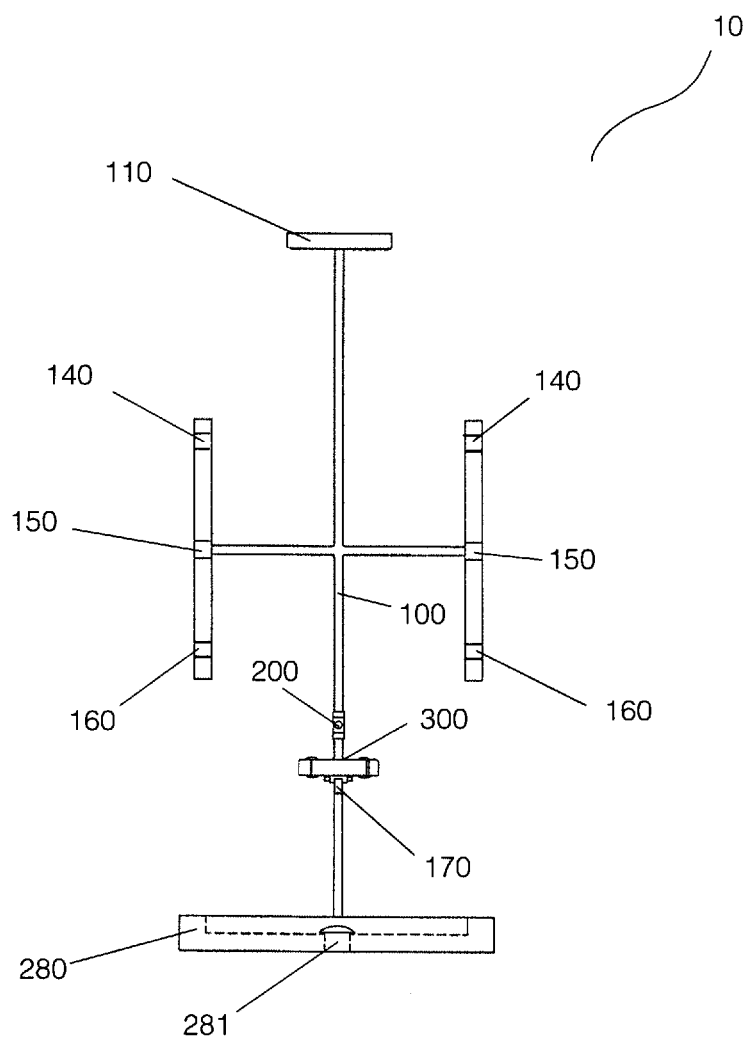
FIG. 21 is a front view of a shower system consistent with a fifth embodiment of the invention.
Figure 22:
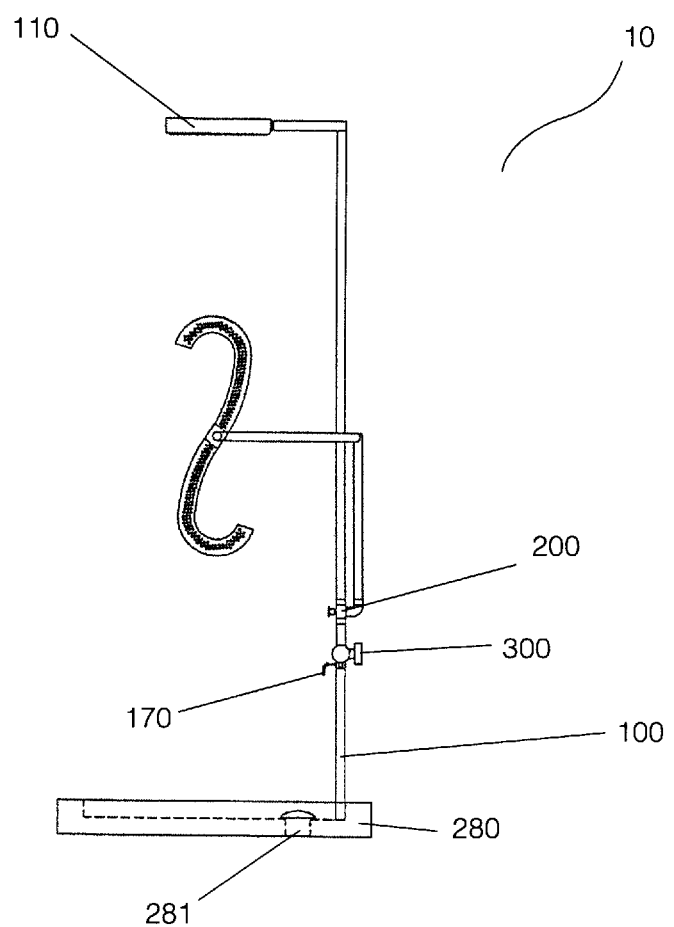
FIG. 22 is a side view of the shower system shown in FIG. 21.

With collective reference to FIGS. 21 to 22, a shower system consistent with a fifth embodiment of the invention is illustrated. The only difference between this embodiment and the first embodiment described above is that the spray spouts corresponding to the shoulders, waist and thighs of the user are all arranged in a "S" shaped tube which fluid-communicates with the main flow passage 100.

Thus, the invention provides a shower system which can provide full body therapy shower experience from head to foot with its individual output application, resulting in enhancing the user's body and feet respectively. As the shower system of the invention is formed with pre-fabricated piping network layout, the user is allowed to install the system quickly and easily on a water faucet in site without the need of specialized and skilled worker and tools. The conduits and fittings of the shower system are all deployed and exposed, which provides the convenient and friendly service and maintenance as well as save the costs in installing and maintaining the in-wall pipes and fittings. The shower system of the invention also avoids the hassle found in extensive cement works and the difficulties in customized in-wall plumbing which incorporates complex piping operation done by the skilled worker.

In addition, the shower system of the invention requires less water and energy when compared with the existing shower systems/apparatuses that need more water and energy for taking a shower. The shower system of the invention only needs to be installed in relatively narrow places, no matter if a bathtub exists or not.

It is understood that many other embodiments of the present invention are also possible, and many corresponding modifications as well as variations can be made by those skills in the art according to the disclosure of the present invention and without departing from the spirits and essentials thereof, while such modifications and variations fall into the scope of the claims of the present invention.

What is claimed is:

1. An exposed shower system comprising:
a main flow passage connected to a water supply;
at least two conduits which are in communication with the main flow passage and connected in pair and horizontally to two sides of the main flow passage;
at least two shower spray spouts in communication with the at least two conduits, and the shower spray spouts being carried at respective outer ends of the conduits;
wherein the conduits are arranged such that the shower spray spouts are in a 180° counter sit relationship with respect to the main flow passage and are combined with the conduits to define a shower stall; and
a diverter means installed on and in communication with the main flow passage for controlling the spray spouts to out-flow water individually or simultaneously and/or for controlling a temperature of the outflow water, the diverter means comprising:
a diverter having a plurality of outputs for directing water to corresponding spray spouts individually or simultaneously; and
a plurality of venturi injection mechanisms corresponding to the number of the outputs of the diverter, said venturi injection mechanisms being disposed at the respective outputs of the diverter and connected to respective flexible hoses, each of said flexible hoses having an end which remains open for introducing air to blend with water coming out from the diverter to produce tiny packets of oxygen bubbles such that said shower spray spouts provide an oxygenating massage function;
wherein the shower system is formed as a completely pre-fabricated one-piece piping network structure, and all parts of the shower system are exposed with respect to a wall and require no wall mount for installation.

2. The shower system as claimed in claim 1, wherein the shower system further comprises a facial spray spout in communication with and disposed at an upper part of the shower system, and a mouth spray spout adjacent to the facial spray spout to provide mouth and gum care to the user.

3. The shower system as claimed in claim 1, wherein the outer end of each of the at least two conduits is connected to a "T"-shaped tube or a "S"-shaped tube on which the shower spray spouts corresponding to shoulders, waist and thighs of the user are arranged.

4. The shower system as claimed in claim 1, wherein the system comprises six conduits symmetrical about the main flow passage to horizontally form 3 pairs of conduits and positioned at different vertical heights so as to correspond to shoulders, waist and thighs of the user, respectively.

5. The shower system as claimed in claim 4, wherein the shower system further comprises a facial spray spout in communication with and disposed at an upper part of the shower system, and a mouth spray spout adjacent to the facial spray to provide mouth and gum care to the user.

6. The shower system as claimed in claim 1, wherein the shower system further comprises an overhead shower spray spout, and a foot spray spout in communication with and disposed at a lower part of the shower system.

7. The shower system as claimed in claim 1, wherein the diverter means comprises a diverter having a plurality of outputs for directing water to the corresponding spray spouts individually or simultaneously, and a built-in venturi injection mechanism connected to an input of the diverter for introducing air, health care fluids or health care powders to blend with water flowing into the diverter, allowing for improving a pressure of water and providing healthy and refreshing shower.

8. The shower system as claimed in claim 7, wherein a mixing valve through which hot and cold water sources flow is included in the diverter means, and the mixing valve is in communication with the built-in venturi injection mechanism.

9. The shower system as claimed in 1, wherein the venturi injection mechanism is used to direct the water output individually to one of the spray spouts corresponding to the head, the face, the mouth, the shoulders, the waist, the thighs and the feet, or to a combination of two or more of these spray spouts.

10. The shower system as claimed in claim 6, wherein a housing is provided to receive the main flow passage and the diverter means.

11. The shower system as claimed in claim 10, wherein health care fluids or health care powders are supplied from a dispenser arranged on the housing.

12. The shower system as claimed in claim 1, wherein the system further comprises a mixing valve through which hot and cold water sources flow into the main flow passage.

13. The shower system as claimed in claim 1, wherein the shower spray spouts are able to rotate by 45° and adjustable for their angles.

14. The shower system as claimed in claim 1, wherein the main flow passage is adjustable vertically for its height to satisfy the preference of a user.

15. The shower system as claimed in claim 1, wherein the connections among the conduits and the main flow passage are accomplished in a threaded manner or in a snap-in manner.

\* \* \* \* \*